(12) United States Patent
Gibson et al.

(10) Patent No.: US 8,711,351 B1
(45) Date of Patent: Apr. 29, 2014

(54) SCATTERING SPECTROSCOPY EMPLOYING HOTSPOT-ALIGNED NANOPORES

(71) Applicant: Hewlett-Packard Development Company, L.P., Houston, TX (US)

(72) Inventors: Gary Gibson, Palo Alto, CA (US); Steven J Barcelo, Mountain View, CA (US); Shih-Yuan Wang, Palo Alto, CA (US); Zhiyong Li, Foster City, CA (US); Huei Pei Kuo, Cupertino, CA (US); Ansoon Kim, Mountain View, CA (US); Alexandre M Bratkovski, Mountain View, CA (US); Zhang-Lin Zhou, Palo Alto, CA (US); Mineo Yamakawa, Campbell, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 13/753,450

(22) Filed: Jan. 29, 2013

(51) Int. Cl.
*G01J 3/44* (2006.01)

(52) U.S. Cl.
USPC .......................................................... 356/301

(58) Field of Classification Search
USPC ................................................ 356/72–73, 301
See application file for complete search history.

(56) References Cited

U.S. PATENT DOCUMENTS

| | | |
|---|---|---|
| 6,743,633 B1 | 6/2004 | Hunter |
| 2010/0245817 A1 | 9/2010 | Park et al. |
| 2011/0166045 A1 | 7/2011 | Dhawan et al. |
| 2012/0162640 A1* | 6/2012 | Sakagami ................ 356/301 |

FOREIGN PATENT DOCUMENTS

WO     2011046706 A1     4/2011

OTHER PUBLICATIONS

Chang et al., "Raman Markers from Silver Nanowire Crossbars," J. Phys. Chem. C., vol. 115, 2011, pp. 4387-4394.

* cited by examiner

*Primary Examiner* — Tarifur Chowdhury
*Assistant Examiner* — Abdullahi Nur

(57) ABSTRACT

Scattering spectroscopy employs a scattering spectroscopy enhancing structure having a hotspot on a first side of a substrate and a nanopore in the substrate, where the nanopore is aligned with the hotspot.

20 Claims, 4 Drawing Sheets

SCATTERING SPECTROSCOPY EMPLOYING HOTSPOT-ALIGNED NANOPORES

CROSS-REFERENCE TO RELATED APPLICATIONS

N/A

STATEMENT REGARDING FEDERALLY SPONSORED RESEARCH OR DEVELOPMENT

N/A

BACKGROUND

Detection and identification (or at least classification) of unknown substances have long been of great interest and have taken on even greater significance in recent years. Among methodologies that hold particular promise for precision detection and identification are various forms of spectroscopy. Spectroscopy may be used to analyze, characterize and identify a substance or material using one or more of an absorption spectrum, a scattering spectrum and an emission spectrum that results when the material is illuminated by a form of electromagnetic radiation (e.g., visible light). The absorption, scattering and emission spectra produced by illuminating the material determine a spectral 'fingerprint' of the material. In general, the spectral fingerprint is characteristic of the particular material to facilitate identification of the material. Among the most powerful of optical emission spectroscopy techniques are those based on Raman scattering.

Scattering spectroscopy is an important means of identifying, monitoring and characterizing a variety of analyte species (i.e., analytes) ranging from relatively simple inorganic chemical compounds to complex biological molecules. Among the various types of scattering spectroscopy are methodologies that exploit Raman scattering and emission due to fluorescence (e.g., fluorescence emission) from an analyte. In general, scattering spectroscopy employs a signal to excite the analyte that, in turn, produces a response or scattered or emitted signal that is dependent on a characteristic (e.g., constituent elements of) the analyte. By detecting and analyzing the scattered or emitted signal (e.g., using spectral analysis), the analyte may be identified and even quantified, in some instances.

BRIEF DESCRIPTION OF THE DRAWINGS

Various features of examples in accordance with the principles described herein may be more readily understood with reference to the following detailed description taken in conjunction with the accompanying drawings, where like reference numerals designate like structural elements, and in which.

Figure 1A:
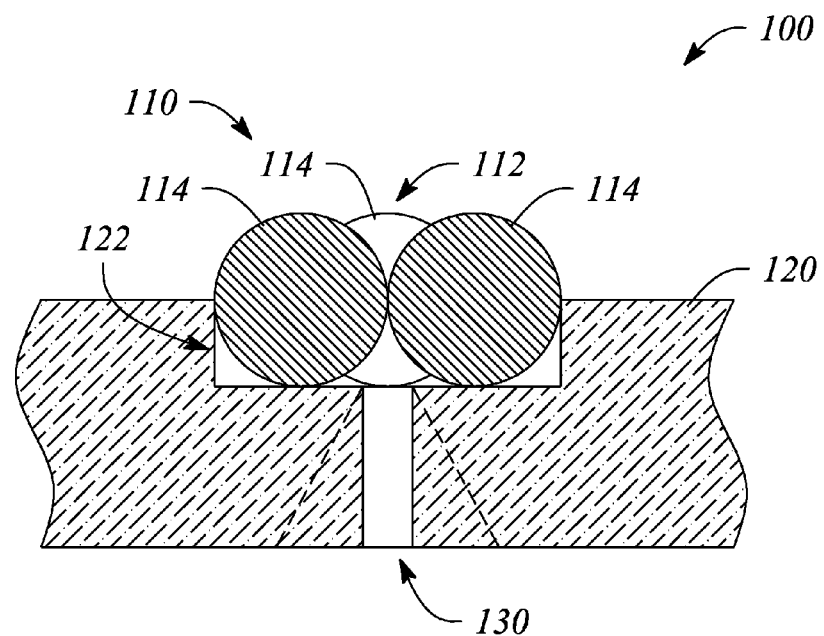
FIG. 1A illustrates a cross sectional view of a scattering spectroscopy apparatus, according to an example consistent with the principles described herein.

Certain examples have other features that are one of in addition to and in lieu of the features illustrated in the above-referenced figures. These and other features are detailed below with reference to the above-referenced figures.

DETAILED DESCRIPTION

Examples in accordance with the principles described herein provide detecting or sensing of various analytes using scattering spectroscopy. In particular, examples in accordance with the principles described herein provide sensing of an analyte using scattering spectroscopy that may one or both of preferentially direct (or deliver) the analyte to a vicinity of a hotspot of the scattering spectroscopy apparatus and selectively stimulate the hotspot. Preferential delivery of the analyte may both enhance scattered signal production as well as improve sensitivity of the scattering spectroscopy, according to various examples. In some examples, the preferential delivery may facilitate single molecule scattering spectroscopy as well as provide one or both of controlled orientation of analyte molecules during sensing and sequential sensing of long-chain analyte molecules. Similarly, selective stimulation of the hotspot during scattering spectroscopy may both increase a scattered signal response from the hotspot and reduce spurious signals from locations other than the hotspot, according to various examples.

Examples of the principles described herein employ scattering spectroscopy to detect or sense the presence of the analyte or a target species. Herein, applicable forms of scattering spectroscopy include substantially any scattering spectroscopy that provides or benefits from the presence of hotspots. For example, applicable forms may include, but are not limited to, surface enhanced Raman spectroscopy (SERS), surface enhanced coherent anti-stokes Raman scattering (SECARS), various spatially offset and confocal versions of Raman spectroscopy, fluorescence spectroscopy (e.g., using fluorescent labels or tags), and direct monitoring of plasmonic resonances. The scattering spectroscopy may provide detection and in some examples, quantification of the analyte. In particular, the detection or sensing may be provided for an analyte that is either adsorbed onto or closely associated with a sensor surface of the scattering spectroscopy apparatus, according to various examples. Herein, 'scattering spectroscopy' will generally be described with reference to Raman-scattering optical spectroscopy for simplicity of discussion and not by way of specific limitation, unless otherwise indicated. Further herein, the term 'scattering spectroscopy' is understood to include spectroscopy that employs signals produced by either or both of scattering processes (e.g., Raman scattering) and emission processes (e.g., fluorescence emission) unless otherwise explicitly noted.

Raman-scattering optical spectroscopy or simply 'Raman spectroscopy', as referred to herein in various forms, employs a scattering spectrum or spectral components thereof produced by inelastic scattering of photons by an internal structure of a material being illuminated. These spectral components contained in a response signal (e.g., a Raman scattering signal) produced by the inelastic scattering may facilitate determination of the material characteristics of an analyte species including, but not limited to, identification of the analyte.

Surface enhanced Raman Spectroscopy (SERS) is a form of Raman spectroscopy that employs a 'Raman-enhancing' surface. SERS may significantly enhance a signal level or intensity of the Raman scattering signal produced by a particular analyte species. In particular, in some instances, the Raman-enhancing surface may include a region associated with nanostructures such as, but not limited to, nanoparticles and nanostructured surfaces and films. In some examples, the nanostructures may include nanofingers or nanorods with or without a Raman-enhancing nanoparticle at a free end thereof. The nanostructures may serve as nanoantennas to one or both of concentrate an illumination field and amplify a Raman emission leading to further enhancement of the strength of the Raman scattering signal, for example. Concentration of the illumination field and amplification of the Raman scattering signal may be associated with plasmonic modes supported by the nanostructures, according to various examples. The plasmonic modes may provide or produce so-called 'hotspots' in a scattering spectroscopy enhancing structure that includes the nanostructures, for example.

Herein, a 'hotspot' is defined with respect to scattering spectroscopy as a region or location on a substrate, or more generally within a scattering spectroscopy enhancing structure, that exhibits a spatially localized enhancement of electromagnetic field. The hotspot may be act as a 'field concentrator' to concentrate and locally enhance an incident electromagnetic field, for example. In various examples, the localized enhancement may be associated with one or both of an incident or stimulus signal (i.e., incident electromagnetic field) used to stimulate the scattering spectroscopy enhancing structure and the production and subsequent radiation of the scattered signal. In particular, at the hotspot, localized electromagnetic fields are enhanced by characteristics of the scattering spectroscopy enhancing structure. The hotspot may be due to spatially localized surface plasmon resonances associated with the scattering spectroscopy enhancing structure, for example. In some examples, the electromagnetic field enhancement due to the hotspot may result in electromagnetic fields that are orders of magnitude higher in a vicinity of the hotspot than in regions outside of the hotspot as well as in an incident electromagnetic wave (e.g., optical stimulus signal). Note that, while a particular structure may represent a hotspot, a hotspot is only 'hot' when in the presence of the incident electromagnetic field, according to various examples.

According to various examples, the electromagnetic field enhancement is associated with physical characteristics of the scattering spectroscopy enhancing structure including, but not limited to, a shape of elements (e.g., nanoparticles or nanostructures) that make up the scattering spectroscopy nanostructure, the materials and material properties (e.g., losses) of the elements, and an arrangement of the elements (e.g., nanoparticles adjacent or nearly adjacent to one another). The electromagnetic field enhancement at the hotspot may also be related to characteristics of the electromagnetic field including, but not limited to, a frequency and an angle of incidence of an excitation signal used to illuminate the hotspot. The electromagnetic field enhancement at the hotspot may, in turn, produce an enhancement of a scattered signal produced by an analyte in a vicinity of the hotspot, according to various examples.

A 'nanoparticle' herein is defined as a nanoscale structure having substantially similar dimensions of length, width and depth. The size of the nanoparticle may range from about 5 nm to about 300 nm in diameter, for example. In some examples, the nanoparticle dimensions may be within a range of about 50 nm to about 100 nm, or about 25 nm to about 100 nm, or about 100 nm to about 200 nm, or about 10 nm to about 150 nm, or about 20 nm to about 200 nm. According to various examples, the shape of a nanoparticle may be a cylinder, a sphere, an ellipsoid, or a faceted sphere or ellipsoid, or a cube, an octahedron, a dodecahedron, or another polygon. The nanoparticle may be a substantially irregular three-dimensional shape, in other examples. In some examples, adjacent nanoparticles may be separated by nanoscale gaps. For example, the gap may range from substantially less than 1 nm to about 5 nm or more. In some examples, the gap may range from about 2 to about 3 nm. In other examples, the gap may range from about 0 nm to about 10 nm.

In some examples, a nanoparticle may be a substantially homogeneous structure. For example, the nanoparticle may be a nanoscale metal particle (e.g., a nanoparticle of gold, silver, copper, etc.). In other examples, the nanoparticle may be a core-shell structure that is substantially inhomogeneous, by definition. For example, the nanoparticle may include a core of a first material that is coated by a second material. The second material of the coating or shell may be a metal while the first material may be either a conductor or a dielectric material. In another example, the second material may be a dielectric and the first material may be a conductor such as a metal, for example. A nanoparticle that is capable of supporting a plasmon (e.g., either a surface plasmon or a bulk plasmon) is defined as a 'plasmonic nanoparticle'. For example, a metal nanoparticle or a metal clad nanoparticle may serve as a plasmonic nanoparticle.

Herein, a 'well' is defined as a depression purpose-formed in a surface. By 'purpose-formed' is it meant that the well is created for an intended purpose as opposed to a depression that may result from damage or as a natural part of a fabrication process that yields the surface. Further by definition herein, the well has an opening at a first end of the well while having a bottom or floor that is substantially closed. However, while being substantially closed at the bottom, the well may have an opening such as a nanopore in the bottom and still be considered a 'well', as will be discussed in more detail below. In general, the nanopore has dimensions that are less than about one half a width of the well, according to various examples. The well has a lateral extent or 'width' defined as a dimension across an opening of the well at the surface into which the well is formed, for example. In some examples, the well may be a nanoscale structure. In particular, the width of the well may be between about 10 nanometers (nm) to greater than about 1000 nm. For example, the well may have a width of about 300 nm to about 400 nm. In another example, the well width is 400 nm to 600 nm. A depth of the well may range from a few nanometers to several hundred nanometers, according to various examples.

A 'nanorod' or equivalently a 'nanofinger' herein is defined as an elongated, nanoscale structure having a length (or height) that exceeds a nanoscale cross sectional dimension (e.g., width) taken in a plane perpendicular to the length, for example. In some examples, the length may exceed by several times the nanoscale cross sectional dimension. In particular, the length of the nanofinger is generally much greater than the nanofinger width (e.g., length>about 2-3 times the width). In some examples, the length may exceed the cross sectional dimension (or width) by more than a factor of 5 or 10.

For example, the width may be about 40 nanometers (nm) and the height may be about 400 nm. In another example, the nanofinger width or diameter may be between about 100 nm and 200 nm and the length may exceed about 500 nm. For example, the width may be about 130-170 nm and the length may be about 500-800 nm. In yet another example, the width at a base of the nanofinger may range between about 20 nm and about 100 nm and the length may be more than about a 1 micrometer (μm). In another example, the nanofinger may be conical with a base having a width ranging from between about 100 nm and about 500 nm and a length or height that may range between about one half (0.5) and several micrometers. According to various examples, the nanofinger may include (e.g., be capped with) a nanoparticle at a distal or free end of the nanofinger. One or both of the entire nanofinger and the nanoparticle at the distal end may be Raman-enhancing, according to some examples.

In various examples, nanofingers may be grown (i.e., produced by an additive process) or produced by etching or a subtractive process. For example, the nanofingers may be grown as nanowires using a vapor-liquid-solid (VLS) growth process. In other examples, nanowire growth may employ one of a vapor-solid (V-S) growth process and a solution growth process. In yet other examples, growth may be realized through directed or stimulated self-organization techniques such as, but not limited to, focused ion beam (FIB) deposition and laser-induced self assembly. In another example, the nanofingers may be produced by using an etching process such as, but not limited to, reactive ion etching, to remove surrounding material leaving behind the nanofingers. In yet other examples, various forms of imprint lithography including, but not limited to, nanoimprint lithography as well as various techniques used in the fabrication of micro-electromechanical systems (MEMS) and nano-electromechanical systems (NEMS) are applicable to the fabrication of the nanofingers and various other elements described herein.

By definition herein, 'nanoscale' means a dimension that is generally less than about 1000 nanometers (nm). For example, a structure or particle that is about 5 nm to about 300 nm in extent is considered a nanoscale structure. Similarly, a slot having an opening size of between about 5 nm and 100 nm is also considered a nanoscale structure, for example.

Further, by definition herein, an 'optical aperture' is a defined as a hole or opening (e.g., a through-hole, waveguide, etc.) through an otherwise optically opaque structure that is capable of transmitting an optical signal or 'light' from a first side to a second side of a structure. In some examples, the optical aperture may be larger than a wavelength in extent or width and transmit the optical signal as a propagating electromagnetic wave. In other examples, the optical aperture may be substantially sub-wavelength in extent in which case the optical signal may be transmitted to the second side as an evanescent wave coupling (e.g., extraordinary optical transmission or near-field coupling). The evanescent wave coupling may be associated with the presence of a surface plasmon at the optical aperture opening on the second side, for example.

Further, as used herein, the article 'a' is intended to have its ordinary meaning in the patent arts, namely 'one or more'. For example, 'a nanopore' means one or more nanopores and as such, 'the nanopore' means 'the nanopore(s)' herein. Also, any reference herein to 'top', 'bottom', 'upper', 'lower', 'up', 'down', 'front', back', 'left' or 'right' is not intended to be a limitation herein. Herein, the term 'about' when applied to a value generally means within the tolerance range of the equipment used to produce the value, or in some examples, means plus or minus 10%, or plus or minus 5%, or plus or minus 1%, unless otherwise expressly specified. Moreover, examples herein are intended to be illustrative only and are presented for discussion purposes and not by way of limitation.

Figure 1B:
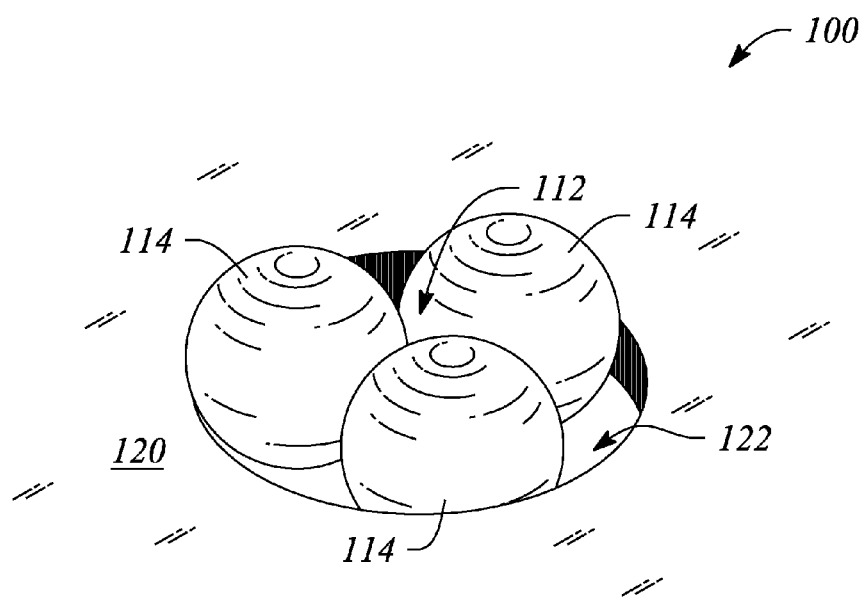
FIG. 1B illustrates a perspective view of the scattering spectroscopy apparatus illustrated in FIG. 1A, according to an example consistent with the principles described herein.
Figure 1C:
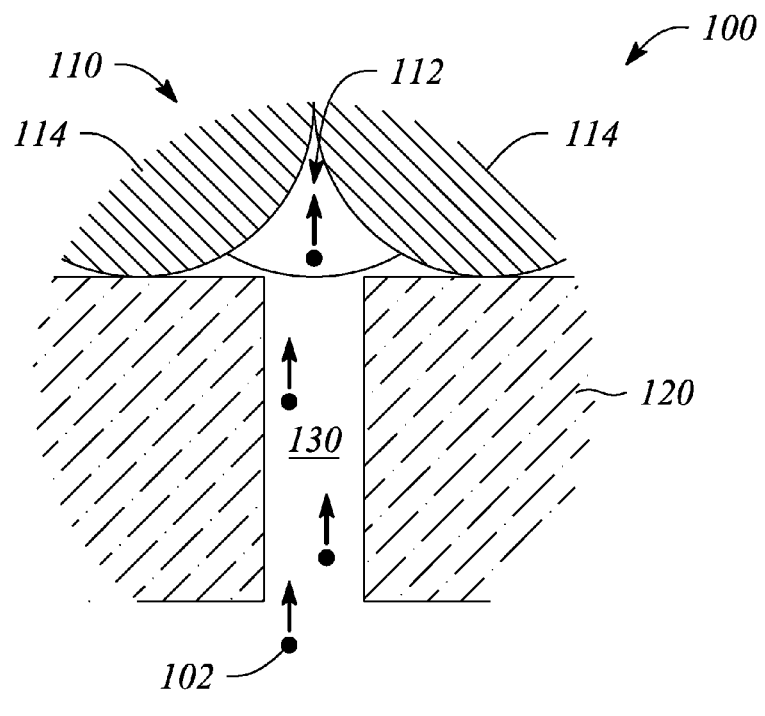
FIG. 1C illustrates a magnified cross sectional view of the scattering spectroscopy apparatus, according to an example consistent with the principles described herein.

FIG. 1A illustrates a cross sectional view of a scattering spectroscopy apparatus 100, according to an example consistent with the principles described herein. FIG. 1B illustrates a perspective view of the scattering spectroscopy apparatus 100 illustrated in FIG. 1A, according to an example consistent with the principles described herein. FIG. 1C illustrates a magnified cross sectional view of the scattering spectroscopy apparatus 100, according to an example consistent with the principles described herein. The scattering spectroscopy apparatus 100 is configured to sense an analyte in a fluid flowing through or adjacent to the scattering spectroscopy apparatus 100 using an optical stimulus signal.

The scattering spectroscopy apparatus 100 includes a scattering spectroscopy enhancing structure 110. In particular, the scattering spectroscopy enhancing structure 110 includes at least one hotspot 112. At the hotspot 112, localized electromagnetic fields are generally enhanced relative to areas outside of the hotspot 112. According to various examples, the electromagnetic field enhancement may be one or both of enhanced electromagnetic fields associated with an incident electromagnetic wave or signal (i.e., the optical stimulus signal) and enhanced electromagnetic fields associated with scattering (e.g., a Raman scattering signal) from the analyte that is located within or in a vicinity of the hotspot 112, for example.

In some examples, the scattering spectroscopy enhancing structure 110 includes a plurality of nanoparticles 114. The hotspot 112 may be located between adjacent ones of the nanoparticles 114, for example, as illustrated in FIGS. 1A and 1B. In other examples, a single nanoparticle 114 may act as the hotspot 112. In some examples, the hotspot 112 may be produced by surface plasmon resonance (SPR) on or supported by the adjacent nanoparticles 114. The SPR may enhance the electromagnetic field in the region between the adjacent nanoparticles 114 to provide the hotspot 112, for example. As such, the nanoparticles 114 also may be referred to as plasmonic nanoparticles 114.

In some examples, the nanoparticles 114 are arranged in ordered groups or multimers, as well as arrays thereof. The adjacent ones of nanoparticles 114 may be members of the ordered group of nanoparticles (e.g., of a dimer, of a trimer, etc.), according to various examples. For example, as illustrated in FIG. 1B, the nanoparticles 114 are arrange as a trimer. The hotspot 112 may be located between the three nanoparticles 114 in the trimer, for example. In some examples, a separate hotspot may be located between each of the three nanoparticles 114 of the trimer. In another example, the nanoparticles 114 may be arranged as a dimer having two nanoparticles 114 adjacent to one another (not illustrated). In various other examples (not illustrated), the nanoparticle multimer may include four, five, six or more nanoparticles 114.

Figure 2:
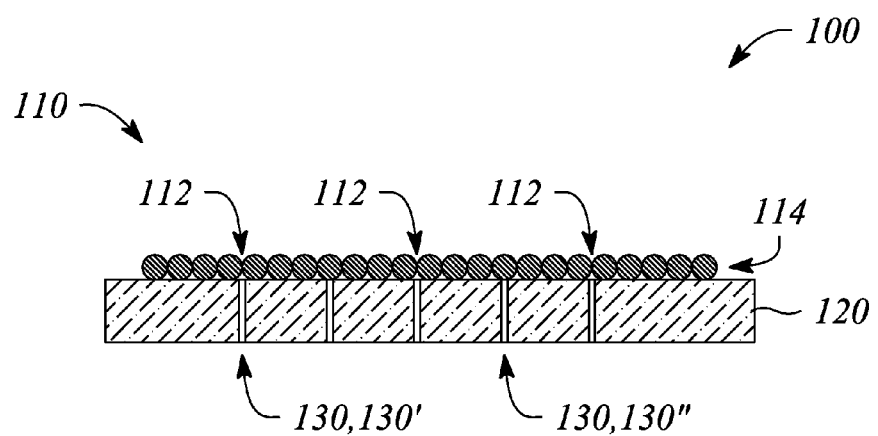
FIG. 2 illustrates a cross sectional view of a scattering spectroscopy apparatus, according to another example consistent with the principles described herein.

In other examples, the plurality of nanoparticles 114 may be arranged as a layer that is substantially without individual or readily identifiable groups or multimers. For example, the plurality of nanoparticles 114 may be deposited, formed or otherwise fabricated (e.g., by selective etching) as a monolayer. FIG. 2 illustrates a cross sectional view of a scattering spectroscopy apparatus 100, according to another example consistent with the principles described herein. In particular, as illustrated in FIG. 2, the scattering spectroscopy enhancing structure 110 includes a plurality of nanoparticles 114 arranged as a monolayer. As illustrated in FIG. 2, the hotspot 112 of the scattering spectroscopy enhancing structure 110 may be located between adjacent nanoparticles 114 of the monolayer. The monolayer may provide a plurality of hotspots 112, for example.

According to various examples, the nanoparticles 114 may include a conductor (i.e., an electrically conductive material). In some examples, the conductor may be a metal such as, but not limited to, gold, silver, platinum, other noble metals, aluminum, copper, as well as an alloy or a mixture of any of these metals with each other or another metal. In some examples, the nanoparticles 114 may include substantially only the conductor. For example, the nanoparticles 114 may be metal nanoparticles 114. In other examples, the conductor (e.g., the metal) may be used to form a surface of the nanoparticles 114. For example, the nanoparticles 114 may include a metal shell surrounding another core material such as, but not limited to a semiconductor or dielectric core material. A conductive surface (e.g., a metal surface) of the nanoparticles 114 may support one or both of a bulk plasmon and a surface plasmon, according to various examples.

When the scattering spectroscopy apparatus 100 is a SERS apparatus 100, the nanoparticles 114 may be configured to enhance Raman scattering and thus be Raman-enhancing nanoparticles of a SERS surface. For example, the nanoparticles 114 may include a material recognized as a Raman-enhancing material (e.g., gold, silver, copper, etc.). In addition, the nanoparticles 114 may incorporate a nanoscale surface roughness, to further enhance Raman scattering or other scattering, for example. In some examples, the nanoparticles 114 may be functionalized to facilitate selective adsorption or binding of the analyte, for example. The nanoparticles may also be functionalized or otherwise coated to maintain a specific gap between adjacent nanoparticles, thereby tuning the properties of the hotspot (e.g. strength of enhancement and resonance wavelength), according to some examples.

According to various examples, the nanoparticles 114 may have any of a variety of shapes. For example, the nanoparticles 114 may be substantially spheroidal in shape (e.g., as illustrated). In other examples, a variety of other shapes may be employed for the nanoparticles 114 including, but not limited to, one or more of oblate spheroids and other ellipsoids, cylinders, pyramids and cones, cubes, octahedrons, and various other polyhedron shapes. The shape of the nanoparticles 114 may influence a shape and strength of the hotspot 112 formed between adjacent nanoparticles 114, according to various examples. In other examples, a combination of the shape and the material of the nanoparticles 114 may influence the shape and strength of the hotspot 112.

In yet other examples, the scattering spectroscopy enhancing structure 110 may include a layer (or film) of material (e.g., a conductor or a metal) that is substantially continuous. Hotspots 112 may be openings in the layer or film. The openings may be nanoscale (e.g., nanopores), in some examples.

Figure 3:
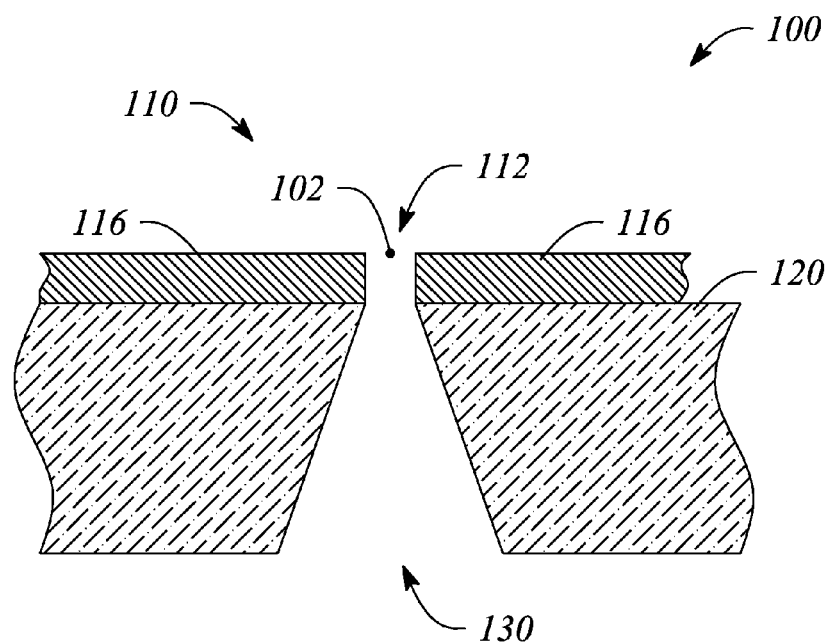
FIG. 3 illustrates a cross sectional view of a scattering spectroscopy enhancing structure, according to an example consistent with the principles described herein.

FIG. 3 illustrates a cross sectional view of a scattering spectroscopy enhancing structure 110 as a substantially continuous layer 116, according to an example consistent with the principles described herein. The scattering spectroscopy enhancing structure 110 illustrated in FIG. 3 includes hotspots 112 formed as openings in the substantially continuous layer 116, for example. As illustrated, the openings that provide the hotspots 112 may be slots formed in the substantially continuous layer 116. The openings in the substantially continuous layer 116 that form the hotspots 112 may be sub-wavelength in extent, according to some examples. For example, the openings may be on the order of a few nanometers to tens of nanometers in extent. The openings may be nanoscale apertures that support near-field or so-called 'extraordinary optical transmission', for example, as described further below, according to some examples.

In various examples, the scattering spectroscopy apparatus 100 further includes a supporting structure or substrate 120. According to some examples, the scattering spectroscopy enhancing structure 110 may be adjacent to a first surface on a first side of the substrate 120. For example, the nanoparticles 114 of the scattering spectroscopy enhancing structure 110 may be supported by and attached to the first surface of the substrate 120, as illustrated in FIGS. 1A, 1B and 2. In another example (not illustrated), the nanoparticles 114 may be connected to an end of a nanofinger or similar elongated nanostructure. The nanofinger may, in turn, be connected to the substrate 120, for example. In another example, the substantially continuous layer 116 may be supported on the first side of the substrate 120, as illustrated in FIG. 3. In yet other examples, the substrate 120 may be integral to the scattering spectroscopy enhancing structure 110. For example, the substrate 120 itself may be the substantially continuous layer or film of the scattering spectroscopy enhancing structure 110 (e.g., not illustrated).

In some examples, the substrate 120 may include a depression or well 122 in the surface of the substrate 120. In some examples, the well 122 may facilitate arranging the plurality of nanoparticles 114 as multimers. FIGS. 1A-1B illustrate the plurality of nanoparticles 114 as a trimer disposed in the well 122, for example. In some examples, the well 122 may have a depth sufficient to facilitate arranging the nanoparticles 114 in the well 122. For example, the well 122 may have a depth that is greater than about 10 percent of mean diameter of the nanoparticles 114. In another example, the well 122 may have a depth that is greater than about 50 percent of the mean diameter of the nanoparticles 114. In yet another example, the well 122 may have a depth between about 20 percent and about 60 percent of the mean diameter. A width or lateral size of the well 122 may be chosen to selectively accommodate the nanoparticle multimer that is to be disposed therein while excluding other (e.g., larger) multimers, according to various examples. For example, the well 120 illustrated in FIGS. 1A-1B has a diameter that is large enough to accommodate the trimer of nanoparticles 114, as illustrated. However, the well 120 illustrated in FIGS. 1A-1B may not be large enough to accommodate a tetramer, for example.

According to various examples, the scattering spectroscopy apparatus 100 further includes a nanopore 130 in the substrate 120. The nanopore 130 is aligned with the hotspot 112 of the scattering spectroscopy enhancing structure 110, according to various examples. By 'aligned' it is meant that the nanopore 130 and hotspot 112 have a predetermined physical relationship to one another, by definition herein. In particular, in some examples, the nanopore 130 is aligned with the hotspot 112 to preferentially direct the analyte into a vicinity of the hotspot 112. In other examples, the nanopore 130 is aligned with the hotspot 112 to selectively provide an optical stimulus signal to the hotspot 112. In yet other examples, the nanopore-hotspot alignment both preferentially directs the analyte and selectively provides the optical stimulus signal to the hotspot 112. In some examples, the nanopore 130 may have a width of between a few nanometers to tens of nanometers. In other examples, the nanopore 130 may be wider than about 100 nanometers but less than about a mean diameter of the nanoparticles 114.

For example, the substrate 120 supports the nanopores 130, as illustrated in FIGS. 1A, 1C and 2. In some examples, the substrate 120 supports the nanopores 130 directly adjacent to the substantially continuous layer 116, as illustrated in FIG. 3, for example. Further, as is variously illustrated in cross section, the nanopore 130 may be aligned to the hotspot 112 formed between adjacent nanoparticles 114, for example. In particular, as illustrated in FIG. 1A, the nanopore 130 may be located in the substrate below the plurality of nanoparticles 114 that form the illustrated nanoparticle trimer, for example, below a collective center of the trimer. In other examples (not illustrated), nanoparticles of one or both of different sizes and different shapes may be used to adjust a location of the hotspot 112 to be in alignment with the nanopore 114.

In another example (not illustrated), the nanopore 130 may be offset from the collective center of the trimer to better align with a hotspot 112 (e.g., a gap) between a selected pair of nanoparticles 114 of the trimer. Alternatively, the nanopore 130 may be located at a hotspot 112 between substantially any pair of nanoparticles 114 in the example monolayer illustrated in FIG. 2. In some examples, the nanopore 130 may be substantially untapered (e.g., as illustrated in cross section in FIGS. 1A, 1C and 2). In other examples, the nanopore 130 may a tapered profile as illustrated by a dashed line in FIG. 1A. FIG. 3 illustrates a tapered nanopore 130 by way of example and not limitation aligned with the hotspot 112 opening in the substantially continuous layer 116.

In some examples, the well 122 may provide a means of establishing the alignment of the nanopore 130 and the plurality of nanoparticles 114, as illustrated in FIG. 1A, for example. In particular, the nanopore 130 may be located in an approximate center of the well 122 such that when the nanoparticles 114 are disposed in the well 122, the hotspot 112 between the nanoparticles 114 aligns with the nanopore 130. According to some examples, the nanoparticles 114 may be selectively deposited in the well 122 using various methods including, but not limited to, one or more of lithographically-directed self-assembly and meniscus force deposition.

In other examples, a number of nanopores 130 may be provided in the substrate 120 along with a relatively large number of adjacent pairs of nanoparticles 114. For example, the relatively large number of adjacent nanoparticle 114 pairs may be provided as a monolayer (e.g., as illustrated in FIG. 2) or as an array of multimers with small spacing, for example. The relatively large number of adjacent pairs of nanoparticles 114 may produce a similarly large number of hotspots 112, for example. Alignment between at least some pairs of nanoparticles 114 and one or more of the nanopores 130 may be reasonably expected, for example. As illustrated in FIG. 2, a first nanopore 130' is aligned between a pair of nanoparticles 114 even though a second nanopore 130" is not, for example. In some examples, a pitch of, or spacing between, a plurality of nanopores 130 may be chosen to correspond a non-integer multiple of a mean diameter of the nanoparticles 114 in a layer, or a non-integer multiple of the spacing between multimers in an array, to increase a probability of alignment, for example. In other examples, locations of the nanopores 130 may be substantially randomly distributed across the substrate 120.

In some examples, the nanopore 130 is a nanoscale hole through the substrate 120. In particular, the nanoscale hole may extend from a second surface to the first surface of the substrate 120. In some examples, the nanoscale through-hole is configured to facilitate passage of the analyte through the substrate 120 and preferentially into the vicinity of the hotspot 112. For example, as illustrated by heavy arrows in FIG. 1C, the analyte 102 may be able to move through the nanopore 130 from the second side to the first side of the substrate 120. Moreover, when the analyte 102 exits the nanopore 130, the analyte 102 is preferentially located either in or inline with (e.g., sufficiently near) the hotspot 112 between the nanoparticles 114, as further illustrated in FIG. 1C. In another example (not illustrated), the analyte 102 may be directed through the nanopore 130 from the first side to the second side in direction opposite that illustrated by the heavy arrows in FIG. 1C. Movement of the analyte 102 through the nanopore 130 in this opposite direction may result in the analyte 102 passing near or through the hotspot 112 prior to entering the nanopore 130, for example.

According to some examples, the scattering spectroscopy apparatus 100 further includes means for moving the analyte through the nanoscale through-hole of the nanopore 130. For example, the scattering spectroscopy apparatus 100 may be configured to provide one or more of an electrostatic force, an electrochemical force, and a concentration gradient to direct the analyte 102 through the nanoscale through-hole. In another example, the means for moving the analyte 102 through the nanopore 130 may include a pressure difference (i.e., a pressure gradient) between the first and second sides of the substrate 120. In yet another example, a fluid flow may provide the means for moving the analyte 102 through the nanoscale through-hole of the nanopore 130.

In some examples, the nanopore 130 is an optical aperture. The nanopore 130 may include the optical aperture in addition to or in lieu of the nanoscale through-hole, according to some examples. The optical aperture is configured to conduct the optical stimulus signal from the second side of the substrate 120 to the first side to preferentially illuminate the scattering spectroscopy enhancing structure 110 at the hotspot 112. Preferential illumination at the hotspot 112 may reduce illumination of other portions of the substrate 120 (e.g., away from the hotspot 112) minimizing excitation of extraneous background or noise signals, according to some examples. For example, the optical aperture of the nanopore 130 may be a segment of optical waveguide that passes through the substrate 120. In another example, the optical aperture of the nanopore 130 may include a lens (e.g., a micro lenslet) to focus the optical stimulus signal on the hotspot 112. In another example, the nanopore 130 includes the nanoscale through-hole that serves as means for conducting the optical stimulus signal (e.g., is also the optical aperture) as well as means for facilitating passage of the analyte 102. In some examples, the optical aperture is a nanoscale optical aperture. In some examples, the nanoscale optical aperture is configured to conduct the optical stimulus signal to the hotspot 112 (i.e., conducting the optical stimulus signal to the scattering spectroscopy enhancing structure 120 to create the hotspot 112) using near-field or evanescent wave coupling.

According to various examples, sensing with the scattering spectroscopy apparatus 100 may include production of a scattered signal through an interaction between the analyte and the optical stimulus signal in the scattering spectroscopy apparatus 100. For example, the scattered signal may include a Raman scattering signal (e.g., due to one or both of Stokes and Anti-Stokes scattering) produced by illuminating the analyte within the scattering spectroscopy apparatus 100 using the optical stimulus signal. When the scattered signal is a Raman scattering signal, the scattering spectroscopy apparatus 100 may provide surface enhanced Raman spectroscopy (SERS) and thus be a SERS apparatus 100, for example. In other examples, the scattered signal may be, but not be limited to, fluorescence emission signal (e.g., as in fluorescence spectroscopy), infrared scattered signal (e.g., as in infrared absorption spectroscopy), and any of a variety of other scattered signals produced by the analyte interacting with the optical stimulus signal. When the scattered signal is or includes analyte fluorescence, the scattering spectroscopy apparatus 100 may be referred to as a fluorescence emission spectroscopy apparatus 100, for example.

Figure 4:
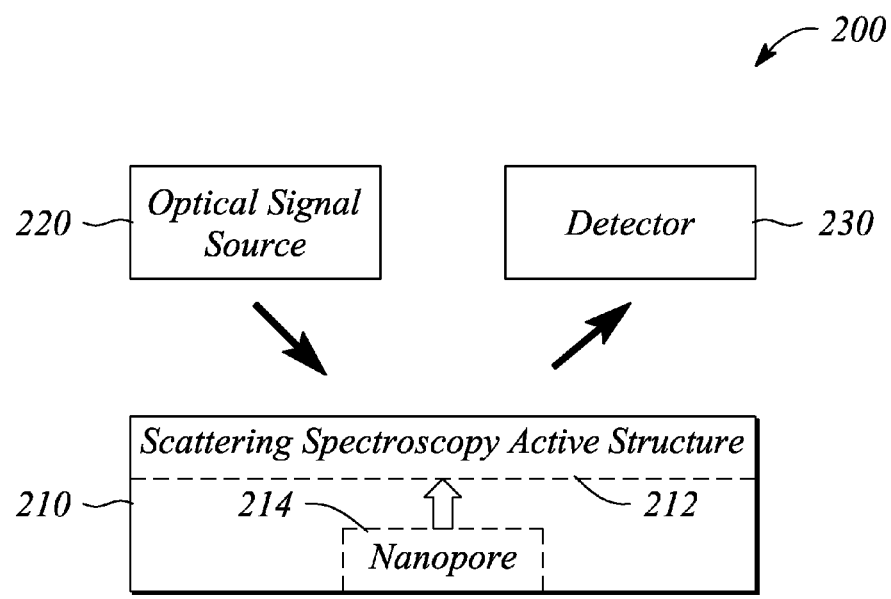
FIG. 4 illustrates a block diagram of a scattering spectroscopy system, according to an example consistent with the principles described herein.

FIG. 4 illustrates a block diagram of a scattering spectroscopy system 200, according to an example consistent with the principles described herein. According to various examples, the scattering spectroscopy system 200 is configured to provide one or both of surface enhanced Raman spectroscopy (SERS) and fluorescence spectroscopy. In other examples, the scattering spectroscopy system 200 may be configured to provide another form of scattering spectroscopy instead of or in addition to SERS and fluorescence spectroscopy.

As illustrated in FIG. 4, the scattering spectroscopy system 200 includes a substrate 210 that includes a scattering spectroscopy enhancing structure 212 on a first side of the substrate and a nanopore 214 in the substrate 210. According to various examples, the nanopore 214 is configured to connect between the first side and a second side of the substrate 210, opposite to the first side. Further, the nanopore 214 is aligned with a hotspot of the scattering spectroscopy enhancing structure 212. The hotspot-aligned nanopore 214 is configured to one or both of preferentially conduct, direct or deliver an analyte into a vicinity of the hotspot and selectively provide an optical stimulus signal to the hotspot.

According to some examples, the substrate 210 may be substantially similar to the scattering spectroscopy apparatus 100, described above. In particular, the scattering spectroscopy enhancing structure 212 may be substantially similar to the scattering spectroscopy enhancing structure 110 and the nanopore 214 may be substantially similar to the nanopore 130, described above. Further, the hotspot-nanopore alignment may be provided in a manner substantially similar to that described above with respect to the scattering spectroscopy apparatus 100.

The scattering spectroscopy system 200 further includes an optical signal source 220. The optical signal source 220 is configured to provide the optical stimulus signal to illuminate the scattering spectroscopy enhancing structure 212. In some examples, the optical signal source 220 includes a laser. In some examples, as illustrated in FIG. 4, the optical signal source 220 is located indirectly adjacent to or associated with (i.e., to illuminate) the first side of the substrate 210. In these examples, the optical stimulus signal provided by the optical signal source 220 may directly illuminate the scattering spectroscopy enhancing structure 212 and the hotspot.

In other examples (not illustrated), the optical signal source 220 is located indirectly adjacent to or associated with (i.e., to illuminate) the second side of the substrate 210. In these examples, the nanopore 214 may be an optical aperture configured to conduct the optical stimulus signal from the optical signal source 220 to the hotspot through the substrate 210 from the second side to the first side. According to some examples, the nanopore 214 is a nanoscale optical aperture. In some examples, the nanoscale optical aperture is configured to conduct the optical stimulus signal to the hotspot using near-field coupling.

In some examples, the nanopore 214 includes a nanoscale hole through the substrate 210 from the second side to the first of the substrate 210. The nanoscale through-hole may be configured to facilitate passage of the analyte through the substrate 210. Further, the passage of the analyte facilitated by the nanoscale through-hole may preferentially conduct the analyte into the vicinity of the hotspot.

In some examples, the first side of the substrate 210 includes a well. The nanopore 214 may be disposed in a bottom of the well, for example. In some examples, the scattering spectroscopy enhancing structure 212 includes a plurality of nanoparticles. In some examples, the plurality of nanoparticles is disposed in the well and arranged around the nanopore 214 to provide the hotspot-nanopore alignment. In some examples, the substrate 210 may include a plurality of nanopores 214. The plurality of nanopores 214 is aligned with a plurality of hotspots in the scattering spectroscopy enhancing structure 212.

In some examples, the scattering spectroscopy system 200 is configured to provide surface enhanced Raman spectroscopy (SERS) and the scattering spectroscopy enhancing structure 212 includes a plurality of Raman-enhancing nanoparticles. In some examples, the Raman-enhancing nanoparticles are arranged on the first side of the substrate 210 adjacent to and in alignment with the nanopore 214. The hotspot may be located between or in a vicinity of adjacent ones of the Raman-enhancing nanoparticles, for example.

In some examples, the scattering spectroscopy system 200 further includes a detector 230. According to various examples, the detector 230 is configured to detect a scattered signal produced by an analyte in a vicinity of the hotspot. The detector 230 may be a spectrometer, for example. In some examples, the detector 230 is located indirectly adjacent to or optically associated with (i.e., in view of) the first side of the substrate 210.

Figure 5:
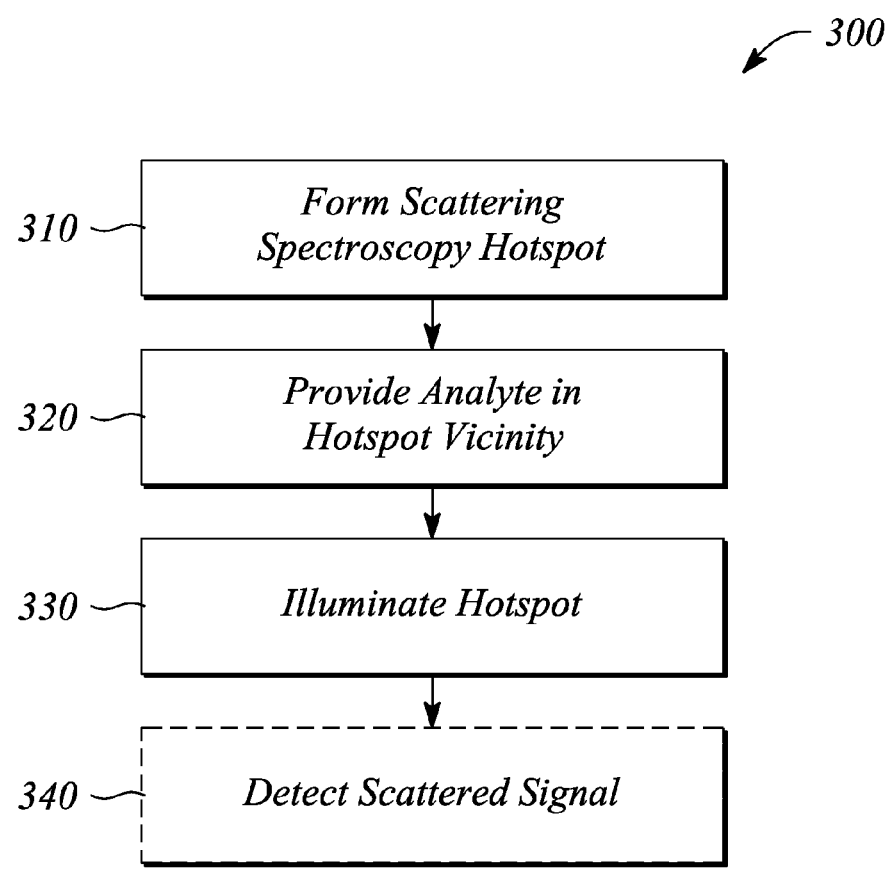
FIG. 5 illustrates a flow chart of a method of scattering spectroscopy, according to an example consistent with the principles described herein.

FIG. 5 illustrates a flow chart of a method of scattering spectroscopy 300, according to an example consistent with the principles described herein. The method 300 of scattering spectroscopy includes forming 310 a scattering spectroscopy hotspot in alignment with a nanopore in a substrate. In some examples, the hotspot is provided by a scattering spectroscopy enhancing structure on a first side of the substrate. In some examples, the scattering spectroscopy hotspot is formed 310 by arranging a plurality of nanoparticles around an opening of the nanopore in the first side of the substrate. In some examples, the plurality of nanoparticles is located in a well in the first side of the substrate. In some examples, the nanopore opening is located in a bottom of the well. In some examples, the nanopore is aligned between a pair of nanoparticles in a monolayer of nanoparticles, or the nanopore is aligned with an opening in substantially continuous nanoparticle layer. In some examples, the scattering spectroscopy enhancing structure is a surface enhanced Raman spectroscopy (SERS) enhancing structure. In some examples, the scattering spectroscopy enhancing structure and hotspot are substantially similar to the scattering spectroscopy apparatus 100, described above.

The method 300 of scattering spectroscopy further includes providing 320 an analyte to a vicinity of the hotspot. In various examples, the analyte is provided into the vicinity of the hotspot by being passed through the nanopore. In some examples, the analyte is provided through the nanopore using one or more of an electrostatic force, an electrochemical force and a concentration gradient.

In some examples, the analyte includes a long-chain molecule such as a polymer having a plurality or a chain of monomers or ligands, for example. For example, the molecule may be a segment or portion of a DNA molecule or a protein. In some examples, the molecule is aligned with the hotspot by passage through the nanopore. In particular, the monomers of the aligned molecule may pass sequentially through the nanopore to the hotspot. The aligned molecule passing through to the hotspot may produce scattered signals indicative of the individual monomers as a result of the aligned passage through the nanopore, according to some examples. In other examples, the alignment of the analyte molecule may facilitate excitation of specific or selected vibrational modes (e.g., Raman modes) within the molecule.

The method 300 of scattering spectroscopy further includes illuminating 330 the hotspot using an optical stimulus signal. Illuminating 330 is configured to produce a scattered signal by way of an interaction between the optical stimulus signal and the analyte in the hotspot vicinity. In some examples, the optical stimulus signal is conducted through the nanopore to illuminate 330 the hotspot. In particular, in some examples, illuminating 330 the hotspot includes illuminating a second side of the substrate and coupling the optical stimulus signal through the nanopore after the analyte is provided 320.

In some examples, the method 300 of scattering spectroscopy further includes detecting 340 the scattered signal using a detector. In some examples, the detector is located on the first side of the substrate. In some examples, the scattered signal is a SERS scattered signal and the method 300 of scattering spectroscopy provides SERS. In other examples, the scattered signal is another scattered signal including, but not limited to, a fluorescence emission signal. In some examples, the method 300 of scattering spectroscopy is performed using the scattering spectroscopy system 200, described above.

Thus, there have been described examples of a scattering spectroscopy apparatus, a scattering spectroscopy system and a method of scattering spectroscopy that employ a nanopore in a substrate that is aligned with a hotspot of a scattering spectroscopy enhancing structure. It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A scattering spectroscopy apparatus comprising:
   a scattering spectroscopy enhancing structure having a hotspot; and
   a nanopore through a substrate, the nanopore being aligned with the hotspot to one or both of preferentially direct an analyte into a vicinity of the hotspot and selectively provide an optical stimulus signal to the hotspot,
   wherein the scattering spectroscopy enhancing structure is adjacent to a first surface on a first side of the substrate, the nanopore to connect between the first side and a second side of the substrate.

2. The scattering spectroscopy apparatus of claim 1, wherein the scattering spectroscopy enhancing structure comprises a plurality of nanoparticles arranged adjacent to the nanopore and the hotspot is located between adjacent ones of the nanoparticles.

3. The scattering spectroscopy apparatus of claim 2, wherein the substrate comprises a well in the first surface of the substrate aligned with the nanopore, the plurality of nanoparticles being disposed in the well.

4. The scattering spectroscopy apparatus of claim 2, wherein the nanoparticles are Raman-enhancing nanoparticles of a surface enhanced Raman spectroscopy (SERS) active surface of the substrate, the scattering spectroscopy apparatus to provide SERS.

5. The scattering spectroscopy apparatus of claim 1, wherein the nanopore comprises a nanoscale hole through the substrate from a second surface to the first surface, the nanoscale through-hole to facilitate passage of the analyte through the substrate and preferentially into the vicinity of the hotspot.

6. The scattering spectroscopy apparatus of claim 5, further comprising means for moving the analyte through the nanoscale through-hole, the means for moving being one or more of an electrostatic force, an electrochemical force and a concentration gradient to preferentially direct the analyte through the nanoscale through-hole.

7. The scattering spectroscopy apparatus of claim 1, wherein the nanopore comprises a nanoscale optical aperture to conduct the optical stimulus signal from a second side of the substrate to the first side to preferentially illuminate the scattering spectroscopy enhancing structure at the hotspot, the nanoscale optical aperture to conduct the optical stimulus signal to the hotspot.

8. A scattering spectroscopy system comprising the scattering spectroscopy apparatus of claim 1, the scattering spectroscopy system further comprising:
   a detector to detect a scattered signal produced by the analyte in the vicinity of the hotspot; and
   an optical signal source to provide the optical stimulus signal.

9. A scattering spectroscopy system comprising:
   a substrate comprising a scattering spectroscopy enhancing structure on a first side of the substrate and a nanopore in the substrate to connect between the first side and a second side of the substrate, the nanopore being aligned with a hotspot of the scattering spectroscopy enhancing structure to one or both of preferentially conduct an analyte into a vicinity of the hotspot and selectively provide an optical stimulus signal to the hotspot;
   a optical signal source to provide the optical stimulus signal to illuminate the scattering spectroscopy enhancing structure; and
   a detector to detect a scattered signal produced by an analyte in the vicinity of the hotspot.

10. The scattering spectroscopy system of claim 9, wherein the optical signal source is located to provide the optical stimulus signal to the second side of the substrate, the nanopore being an optical aperture to conduct the optical stimulus signal to the hotspot through the substrate from the second side to the first side.

11. The scattering spectroscopy system of claim 9, wherein the nanopore comprises a nanoscale hole through the substrate from the second side to the first side of the substrate, the nanoscale through-hole to facilitate passage of the analyte through the substrate and preferentially into the vicinity of the hotspot.

12. The scattering spectroscopy system of claim 9, wherein the first side of the substrate comprises a well with the nanopore disposed in a bottom of the well, the scattering spectroscopy enhancing structure comprising a plurality of nanoparticles disposed in the well and arranged around the nanopore to provide a hotspot-nanopore alignment.

13. The scattering spectroscopy system of claim 9, wherein the substrate comprises a plurality of nanopores aligned with a plurality of hotspots in the scattering spectroscopy enhancing structure.

14. The scattering spectroscopy system of claim 9, wherein the scattering spectroscopy enhancing structure comprises a plurality of Raman-enhancing nanoparticles arranged adjacent to the nanopore on the first side of the scattering spectroscopy substrate, the hotspot being located between adjacent ones of the Raman-enhancing nanoparticles, the scattering spectroscopy system to provide surface enhanced Raman spectroscopy (SERS).

15. A method of scattering spectroscopy, the method comprising:
    forming a scattering spectroscopy hotspot in alignment with a nanopore in a substrate, the scattering spectroscopy hotspot being provided by a scattering spectroscopy enhancing structure on a first side of the substrate;
    providing an analyte to a vicinity of the hotspot; and illuminating the hotspot using an optical stimulus signal to produce a scattered signal through an interaction between the optical stimulus signal and the analyte in the hotspot vicinity, wherein one or both of the analyte is provided from a second side of the substrate opposite to the first side by passing through the nanopore and the optical stimulus signal is conducted from a second side through the nanopore to illuminate the hotspot.

16. The method of scattering spectroscopy of claim 15, wherein the analyte is provided by being passed through the nanopore using one or more of an electrostatic force, an electrochemical force and a concentration gradient.

17. The method of scattering spectroscopy of claim 16, wherein an analyte comprising a molecule having a plurality of monomers is aligned by passage through the nanopore, monomers of the plurality passing sequentially through the hotspot to produce scattered signals indicative of the monomers.

18. The method of scattering spectroscopy of claim 15, wherein the scattering spectroscopy hotspot is formed by arranging a plurality of nanoparticles around an opening of the nanopore in the first side of the substrate, the plurality of nanoparticles being located in a well in the first side of the substrate and the nanopore opening being located in a bottom of the well.

19. The method of scattering spectroscopy of claim 15, wherein illuminating the hotspot comprises illuminating the second side of the substrate and coupling the optical stimulus signal through the nanopore, and wherein the method further comprises detecting the scattered signal from the first side of the substrate using a detector.

20. The method of scattering spectroscopy of claim 15, wherein the scattering spectroscopy enhancing structure is a surface enhanced Raman spectroscopy (SERS) enhancing structure, the scattered signal being a SERS scattered signal.

* * * * *